United States Patent
Franzosi et al.

(10) Patent No.: US 9,234,221 B2
(45) Date of Patent: Jan. 12, 2016

(54) PROCESS FOR THE PRODUCTION OF LIPIDS FROM BIOMASS

(75) Inventors: Giuliana Franzosi, Novara (IT); Francesca Pizza, Milan (IT); Daniela Cucchetti, Cuggiono (IT); Daniele Bianchi, Arese (IT); Concetta Maria Compagno, Spino d'Adda (IT); Silvia Galafassi, Verbania (IT)

(73) Assignee: ENI S.P.A., Rome (IT)

( * ) Notice: Subject to any disclaimer, the term of this patent is extended or adjusted under 35 U.S.C. 154(b) by 284 days.

(21) Appl. No.: 13/880,610

(22) PCT Filed: Oct. 14, 2011

(86) PCT No.: PCT/EP2011/068043
§ 371 (c)(1),
(2), (4) Date: Jul. 8, 2013

(87) PCT Pub. No.: WO2012/052368
PCT Pub. Date: Apr. 26, 2012

(65) Prior Publication Data
US 2013/0289289 A1 Oct. 31, 2013

(30) Foreign Application Priority Data
Oct. 22, 2010 (IT) .............................. MI2010A1951

(51) Int. Cl.
*C11B 1/00* (2006.01)
*C12P 7/64* (2006.01)
*C10L 1/02* (2006.01)

(52) U.S. Cl.
CPC ................. *C12P 7/64* (2013.01); *C12P 7/6463* (2013.01); *C10L 1/026* (2013.01); *C10L 2290/26* (2013.01); *C10L 2290/548* (2013.01); *C12P 2203/00* (2013.01); *Y02E 50/13* (2013.01)

(58) Field of Classification Search
CPC ............ C11B 1/12; C11B 1/00; C11B 1/104; C11B 1/02; B01D 11/0203; C12P 7/6472; C12P 7/6427; C12P 7/6463; C12P 7/6454; A23D 9/00
USPC ............................................... 554/8; 435/134
See application file for complete search history.

(56) References Cited

FOREIGN PATENT DOCUMENTS

WO    2004015120 A1    2/2004
WO    WO 2004015120 A1 *    2/2004
(Continued)

OTHER PUBLICATIONS

Kootstra et al: "Comparison of dilute mineral and organic acid pretreatment for enzymatic hydrolysis of wheat straw", Biochemical Engineering Journal, vol. 46, No. 2, Oct. 1, 2009, pp. 126-1 31.*
(Continued)

*Primary Examiner* — Deborah D Carr
(74) *Attorney, Agent, or Firm* — Tarolli, Sundheim, Covell & Tummino LLP (57) ABSTRACT

Process for the production of lipids from biomass comprising polysaccharides. The biomass is subjected to acid hydrolysis to obtain a solid phase and an aqueous phase. The solid phase is subjected to acid or to enzymatic hydrolysis obtaining a further solid phase and a further aqueous phase. The aqueous phases obtained from both hydrolysis steps are subjected to fermentation with an oleaginous yeast. The obtained fermentation broth comprises oleaginous cellular biomass which is subjected to microfiltration for the isolation of lipids. Said lipids can be used in the production of biodiesel or green diesel.

30 Claims, 2 Drawing Sheets

(56) References Cited

FOREIGN PATENT DOCUMENTS

WO          2010069516  A2      6/2010
WO     WO 2010069516  A2  *    6/2010

OTHER PUBLICATIONS

Dai et al: "Biodiesel generation From oleaginous yeast *Rhodotorula glutinis* with xylose assimilating capacity", African Journal of Biotechnology, vol. 6, No. 18, Sep. 1, 2007, pp. 2130-2134.*

Rivard et al: "Measurement of the inhibitory potential and detoxification of biomass pretreatment hydrolysate for ethanol production", Applied Biochemistry and Biotechnology, vol. 57-58, Jan. 1, 1996, pp. 183-191.*

Kootstra, A.M., et al., "Comparison of dilute mineral and organic acid pretreatment for enzymatic hydrolysis of wheat straw", Biomedical Engineering Journal, vol. 46, No. 2, Oct. 1, 2009, pp. 126-131.

Dai Chuan-Chao, et al., "Biodiesel generation from oleaginous yeast *Rhodoturula glutinis* with xylose assimilating capacity", African Journal of Biotechnology, Academic Press, US, vol. 6, No. 18, Sep. 1, 2007, pp. 2130-2134.

Rivard, C.J., et al., "Measurement of the inhibitory potential and detoxification of biomass pretreatment hydrolysate for ethanol production", Applied Biochemistry and Biotechnology, The Humana Press, Inc., US, vol. 57-58, Jan. 1, 1996, pp. 183-191.

* cited by examiner

PROCESS FOR THE PRODUCTION OF LIPIDS FROM BIOMASS

RELATED APPLICATION

This application is a National Phase filing of PCT/EP2011/068043, filed Oct. 14, 2011, and claims priority to Italian Application No. MI2010A001951, filed Oct. 22, 2010, the subject matter of which are incorporated herein by reference in their entirety.

The present invention relates to a process for the production of lipids from biomass, including at least one polysaccharide.

More specifically, the present invention relates to a process for the production of lipids from biomass including at least one polysaccharide which comprises subjecting said biomass including at least one polysaccharide to acid hydrolysis obtaining a solid phase and an aqueous phase, subjecting said solid phase to acid hydrolysis or to enzymatic hydrolysis obtaining a further solid phase and a further aqueous phase, subjecting the aqueous phases obtained from said hydrolyses to fermentation in the presence of at least one oleaginous yeast obtaining a fermentation broth comprising an oleaginous cellular biomass, subjecting at least a part of said fermentation broth to microfiltration.

The lipids thus obtained can be advantageously used in the production of biodiesel or green diesel which can be used as such or in a mixture with other fuels for motor vehicles.

Generally speaking, a biomass is any substance with an organic, vegetable or animal matrix, which can be destined for energy purposes, for example as raw material for the production of biofuels or components which can be added to fuels. Biomass can therefore form a renewable energy source as an alternative to traditional raw materials of a fossil origin, normally used in the production of fuels. For this purpose, lignocellulosic biomass is particularly useful.

The production of sugars from biomass, in particular lignocellulosic biomass, is known in the art.

Lignocellulosic biomass is a complex structure comprising three main components: cellulose, hemicellulose and lignin. Their relative quantities vary according to the type of lignocellulosic biomass used. In the case of plants, for example, said quantities vary according to the species and age of the plant.

Cellulose is the greatest constituent of lignocellulosic biomass and is generally present in quantities ranging from 30% by weight to 60% by weight with respect to the total weight of the lignocellulosic biomass. Cellulose consists of glucose molecules (from about 500 to 10,000 units) bound to each other through a β-1,4 glucoside bond. The establishment of hydrogen bonds between the chains causes the formation of crystalline domains which give resistance and elasticity to vegetal fibres. In nature, it can only be found in its pure state in annual plants such as cotton and flax, whereas in ligneous plants it is always accompanied by hemicellulose and lignin.

Hemicellulose, which is generally present in a quantity ranging from 10% by weight to 40% by weight with respect to the total weight of the lignocellulosic biomass appears as a mixed polymer, relatively short (from 10 to 200 molecules) and branched, made up of both sugars with six carbon atoms (glucose, mannose, galactose) and also sugars with five carbon atoms (xylose, arabinose). Some important properties of vegetal fibres are due to the presence of hemicellulose, of which the main property is that of favouring the imbibition of said vegetal fibres, when water is present, causing their swelling. Hemicellulose also has adhesive properties and therefore tends to harden or to develop a horny consistency, with the consequence that said vegetal fibres become rigid and are imbibed more slowly.

Lignin is generally present in a quantity ranging from 10% by weight to 30% by weight with respect to the total weight of the lignocellulosic biomass. Its main function consists in binding and cementing the various vegetal fibres with each other giving the plant compactness and resistance and also provides protection against insects, pathogen agents, lesions and ultraviolet light. It is mainly used as fuel but is also currently widely used in industry as a dispersant, hardener, emulsifying agent, for plastic laminates, cartons and rubber products. It can also be chemically treated to produce aromatic compounds, of the vanillin, syringaldehyde, p-hydroxybenzaldehyde type, which can be used in pharmaceutical chemistry, or in the cosmetic and food industry.

In order to optimize the transformation of lignocellulosic biomass into products for energy use, subjecting said lignocellulosic biomass to a preliminary treatment to separate the lignin and hydrolyze the cellulose and hemicellulose to simple sugars, such as, for example, glucose and xylose, is known. Said sugars can be used as carbon sources in fermentation processes in the presence of micro-organisms for the production of alcohols and/or lipids.

Patent application US 2008/0102176, for example, describes a method for the extraction of vegetable fats comprising: pulverizing the raw material containing cellulose in order to obtain particles with a diameter of 1 mm-2 mm; immerging the particles in sulfuric acid at a concentration equal to 1%-2% to acidify said particles in order to increase the hydrolysis of the cellulose and to regulate the pH to a value of 4.5±0.5; removing the particles acidified by the sulfuric acid, and adding, in sequence, cellulase and an oleaginous yeast to the acidified particles and subjecting to fermentation for 8-9 days at a temperature of 25° C.-30° C. and a humidity of 85%-90%; adding an aliphatic hydrocarbon, as solvent, to the fermentation products in order to extract the fats, obtaining an extraction mixture; removing the acidified particles remaining in the extraction mixture and separating the fats from the solvent by distillation, obtaining raw oil. The cellulase is preferably obtained from *Trichoderma viride* and the oleaginous yeast is *Rhodotorula glutinis*. The fats obtained can be converted to biodiesel, after esterification.

Dai et al., describe the production of biodiesel from oleaginous yeasts in the article: "Biodiesel generation from oleaginous yeast *Rhodotorula glutinis* with xylose assimilating capacity", published in "African Journal of Biotechnology" (2007), Vol. 6 (18), pages 2130-2134. In this article, the lignocellulosic biomass is ground and subjected to acid hydrolysis in the presence of sulfuric acid. The sugars thus obtained are used as carbon sources in a fermentation process in the presence of a previously selected strain of *Rhodotorula glutinis*, capable of also using pentoses, xylose in particular, with the purpose of obtaining oils which are subsequently extracted by Soxhlet extraction and subjected to transesterification in order to obtain biodiesel.

The above processes however can have various drawbacks. The yield of sugars obtained from the treatment of the lignocellulosic biomass with diluted sulfuric acid (i.e. acid hydrolysis), in particular glucose, for example, is generally low (e.g., lower than 50%). Furthermore, the use of the sugars obtained from said treatment as carbon sources in the fermentation process in the presence of oleaginous yeasts is not always capable of giving good yields of lipids [e.g., yields of lipids lower than 30% by weight, said yield being calculated as the total quantity of lipids present in the oleaginous cellular biomass (dry) obtained after fermentation].

Furthermore, in order to obtain a good yield of sugars from the hydrolysis and a good yield of lipids from the fermentation [e.g., yield of lipids higher than or equal to 40%, said yield being calculated as the total quantity of lipids present in the oleaginous cellular biomass (dry) obtained after fermentation], said processes require the use of high concentrations of lignocellulosic biomass in the hydrolysis step. The use of high concentrations of lignocellulosic biomass, moreover, in particular in the case of acid hydrolysis of the lignocellulosic biomass, can lead to the formation of high quantities of toxic compounds such as, for example, furfural, hydroxymethylfurfural, phenol compounds, which can act as growth inhibitors of the microorganisms normally used in the subsequent fermentation processes of the sugars and, consequently, of the production of lipids.

The Applicant has now found that the production of lipids from biomass including at least one polysaccharide, can be advantageously carried out by means of a process which comprises subjecting said biomass including at least one polysaccharide to acid hydrolysis obtaining a solid phase and an aqueous phase, subjecting said solid phase to acid hydrolysis or to enzymatic hydrolysis obtaining a further solid phase and a further aqueous phase, subjecting the aqueous phases obtained from said hydrolysis to fermentation in the presence of at least one oleaginous yeast obtaining a fermentation broth comprising an oleaginous cellular biomass, subjecting a part of said fermentation broth to microfiltration.

Numerous advantages can be obtained by means of said process. Said process, for example, allows sugars to be obtained, in particular pentoses from the acid hydrolysis treatment of the biomass including at least one polysaccharide and hexoses deriving from the acid or enzymatic hydrolysis treatment of the solid phase obtained from said acid hydrolysis treatment of the biomass including at least one polysaccharide, which can be subsequently used as carbon sources in the fermentation process for the production of lipids, in two distinct fermentation phases. In particular the pentoses obtained from the acid hydrolysis treatment of the biomass including at least one polysaccharide can be used for obtaining a good growth of the oleaginous cellular biomass, whereas the hexoses obtained from the acid or enzymatic hydrolysis treatment of the solid phase obtained from said acid hydrolysis treatment of the biomass including at least one polysaccharide, can be used for increasing the yield of lipids. Furthermore, the microfiltration of at least a part of the fermentation broth allows the volume of said fermentation broth to be kept constant in the fermentation device and to increase the concentration of oleaginous cellular biomass in said fermentation broth, even when feeding diluted solutions of sugars deriving from the acid hydrolysis of the biomass including at least one polysaccharide, and/or from the acid or enzymatic hydrolysis treatment of the solid phase obtained from said acid hydrolysis treatment of the biomass including at least one polysaccharide. Said process allows lipids to be obtained with a high yield [e.g., yield of lipids higher than or equal to 40%, said yield being calculated as the total quantity of lipids present in the oleaginous cellular biomass (dry) obtained after fermentation]. Said lipids can be advantageously used in the production of biodiesel or green diesel which can be used as such, or in a mixture with other fuels for motor vehicles.

An object of the present invention therefore relates to a process for the production of lipids from biomass including at least one polysaccharide, comprising:

subjecting said biomass, including at least one polysaccharide to acid hydrolysis obtaining a first mixture comprising a first solid phase and a first aqueous phase;

feeding said first aqueous phase to a fermentation device in the presence of at least one oleaginous yeast obtaining a first fermentation broth comprising a first oleaginous cellular biomass;

subjecting said first solid phase to acid hydrolysis or to enzymatic hydrolysis obtaining a second mixture comprising a second solid phase and a second aqueous phase;

feeding said second aqueous phase to said fermentation device in the presence of said first fermentation broth obtaining a second fermentation broth comprising a second oleaginous cellular biomass including lipids;

subjecting at least a part of said second fermentation broth to microfiltration obtaining a retentate and a permeate;

feeding said retentate to said fermentation devices.

For the purposes of the present description and of the following claims, the definition of the numerical ranges always include extremes, unless otherwise specified.

In accordance with a preferred embodiment of the present invention, said polysaccharide can be selected from cellulose, hemicellulose, or mixtures thereof. Cellulose, or mixtures of hemicellulose and cellulose, are particularly preferred.

In accordance with a further preferred embodiment of the present invention, said biomass including at least one polysaccharide is a lignocellulosic biomass. As mentioned above, the lignocellulosic biomass includes three components: hemicellulose, cellulose and lignin.

Said lignocellulosic biomass is preferably selected from:
- products of crops expressly cultivated for energy use (for example, miscanthus, foxtail millet, common cane), including waste products, residues and scraps of said crops or of their processing;
- products of agricultural cultivations, forestation and silviculture, comprising wood, plants, residues and waste products of agricultural processing, of forestation and of silviculture;
- waste of agro-food products destined for human nutrition or zootechnics;
- residues, not chemically treated, of the paper industry;
- waste products coming from the differentiated collection of solid urban waste (e.g., urban waste of a vegetable origin, paper).

In accordance with a preferred embodiment of the present invention, said biomass including at least one polysaccharide can be subjected to a preliminary grinding process before being subjected to said acid hydrolysis. Said biomass including at least one polysaccharide can preferably be ground until particles having a diameter ranging from 0.1 mm to 10 mm, more preferably ranging from 0.5 mm to 4 mm, are obtained. Particles having a diameter of less than 1 mm are particularly preferred.

According to a preferred embodiment of the present invention, said acid hydrolysis can be carried out in the presence of an aqueous solution of at least one inorganic acid.

According to a preferred embodiment of the present invention, said biomass including at least one polysaccharide or said first solid phase can be present in the reaction mixture in a quantity ranging from 5% by weight to 20% by weight, preferably from 10% by weight to 18% by weight, with respect to the total weight of the reaction mixture.

For the purposes of the present description and of the following claims, the term "reaction mixture" means, in the case of acid hydrolysis, the mixture comprising said biomass including at least one polysaccharide or said first solid phase and said aqueous solution of said at least one inorganic acid.

For the purposes of the present description and of the following claims, the term "reaction mixture" means, in the case of enzymatic hydrolysis, the mixture comprising said first solid phase and an aqueous solution of at least one enzyme.

According to a preferred embodiment of the present invention, said inorganic acid can be selected from sulfuric acid, nitric acid, hydrochloric acid, phosphoric acid, or mixtures thereof. Sulfuric acid is preferred.

According to a preferred embodiment of the present invention, said inorganic acid is present in said aqueous solution at a concentration ranging from 0.1% by weight to 2% by weight, preferably ranging from 0.3% by weight to 1% by weight, with respect to the total weight of the aqueous solution.

Said inorganic acid acts as catalyst for the acid hydrolysis of said biomass including at least one polysaccharide, or of said first solid phase. In particular, when the biomass including at least one starting polysaccharide is a lignocellulosic biomass, said inorganic acid specifically acts as catalyst for the acid hydrolysis of the hemicellulose.

According to a preferred embodiment of the present invention, said acid hydrolysis can be carried out at a temperature ranging from 140° C. to 270° C., preferably ranging from 170° C. to 250° C.

According to a preferred embodiment of the present invention, said acid hydrolysis can be carried out for a time ranging from 10 seconds to 30 minutes, preferably from 30 seconds to 20 minutes.

Said acid hydrolysis can be carried out in reactors known in the art, such as, for example, autoclaves, or extruders.

Said enzymatic hydrolysis can be carried out according to techniques known in the art described, for example, in American patents U.S. Pat. No. 5,628,830, 5,916,780 and 6,090,595, using commercial enzymes such as, for example, Celluclast 1.5 L (Novozymes), Econase CE (Rohm Enzymes), Spezyme (Genecor), Novozym 188 (Novozymes), used individually or in mixture with each other.

If said biomass including at least one polysaccharide or said first solid phase are subjected to acid hydrolysis, in order to reduce the quantity of by-products such as, for example, furfural, hydroxymethylfurfural, phenol compounds, which can act as growth inhibitors of the oleaginous yeast used in the subsequent fermentation and, consequently, of the production of lipids, said first aqueous phase and/or said second aqueous phase can be subjected to treatment with at least one adsorbing material.

According to a further preferred embodiment of the present invention, said first aqueous phase and/or said second aqueous phase can be subjected to treatment with at least one adsorbing material obtaining a third aqueous phase and/or a fourth aqueous phase, respectively.

Said first solid phase and said first aqueous phase, as well as said second solid phase and said second aqueous phase, can be separated by means of techniques known in the art such as, for example, filtration, centrifugation. Said phases are preferably separated by filtration.

In order to bring the pH to acceptable values for the subsequent fermentation, it can be advantageous to subject said first aqueous phase and/or said second aqueous phase to neutralization.

According to a preferred embodiment of the present invention, before being fed to said fermentation device, or before being subjected to said treatment with at least one adsorbing material, said first aqueous phase and/or said second aqueous phase, can be subjected to neutralization by the addition of at least one oxide and/or of at least one hydroxide such as, for example, calcium oxide, calcium hydroxide, or barium hydroxide, or mixtures thereof.

The salts which are formed after said addition can be separated from said first aqueous phase or from said second aqueous phase, by means of techniques known in the art such as, for example, filtration, centrifugation. Said salts are preferably separated by filtration.

Said second solid phase, comprising lignin, can be upgraded as fuel, for example as fuel for producing the energy necessary for sustaining the treatment processes of the biomass including at least one polysaccharide.

According to a preferred embodiment of the present invention, said treatment with at least one adsorbing material can be carried out at a temperature ranging from 10° C. to 150° C., preferably ranging from 20° C. to 100° C.

According to a preferred embodiment of the present invention, said treatment with at least one adsorbing material can be carried out at a pressure ranging from 0.5 bar to 10 bar, preferably ranging from 0.8 bar to 2 bar.

According to a preferred embodiment of the present invention, said treatment with at least one adsorbing material can be carried out for a time ranging from 10 minutes to 6 hours, preferably ranging from 30 minutes to 5 hours.

At the end of said treatment with at least one adsorbing material, said adsorbing material can be separated from said third aqueous phase or from said fourth aqueous phase, by means of techniques known in the art such as, for example, filtration, centrifugation. Said adsorbing material is preferably separated by filtration.

For the purposes of the present description and of the following claims, the term "adsorbing material" means a material, natural or synthetic, capable of withholding organic substances on its surface through physical or chemical means ("chemisorption")

According to a preferred embodiment of the present invention, said adsorbing material can be selected from microporous crystalline silicates or metallo-silicates of the zeolitic type having, for example, MFI, MOR, FAU, or BEA structures.

Specific examples of microporous crystalline silicates and of metallo-silicates of the zeolitic type which can be advantageously used for the purposes of the present invention are the zeolites CBV2314 (of the MFI type with a Si/Al ratio=12) and CBV 28014 (of the MFI type with a Si/Al ratio=140) of Zeolyst International.

According to a preferred embodiment of the present invention, said adsorbing material can be added to said first aqueous phase and/or to said second aqueous phase, in a quantity ranging from 0.5% by weight to 50% by weight, preferably ranging from 3% by weight to 15% by weight, with respect to the total weight of said first aqueous phase or of said second aqueous phase.

Said treatment with at least one adsorbing material can be carried out in reactors known in the art such as, for example, stirred reactors, fixed bed reactors, slurry reactors.

Said treatment with at least one adsorbing material can be carried out in different ways such as, for example, batchwise or in continuous.

It should be noted that said treatment with at least one adsorbing material reduces the content of by-products, in particular furfural, hydroxymethyl-furfural, phenol compounds, which can be formed during the acid hydrolysis of said biomass including at least one polysaccharide and/or of said first solid phase and that, as indicated above, can act as growth inhibitors of the oleaginous yeast used in the above fermentation and, consequently, of the production of lipids. In particular, after said treatment with at least one adsorbing material, said third aqueous phase and said fourth aqueous phase have a content of furfural and of hydroxymethylfurfural lower than or equal to 0.1 g/l.

It is also to be noted that said treatment with at least one adsorbing material does not cause a significant reduction in the carbon source present in said first aqueous phase or in said second aqueous phase. Said third aqueous phase and said fourth aqueous phase generally have a total organic carbon content ("Total Organic Carbon"—TOC) equal to about 90% with respect to the total organic carbon content ("Total Organic Carbon"—TOC) of said first aqueous phase or of said second aqueous phase, respectively. Said total organic carbon ("Total Organic Carbon"—TOC) was determined by combustion by means of a TOC analyzer capable of determining the total carbon content ("total carbon"—TC) and the inorganic carbon content ("inorganic carbon"—IC) from which the total organic carbon content ("Total Organic Carbon"—TOC) is calculated, by difference.

It should therefore be noted that the content of organic material of said third aqueous phase or of said fourth aqueous phase remains substantially unvaried with respect to that of said first aqueous phase or of said second aqueous phase, respectively.

According to a preferred embodiment of the present invention, said first solid phase comprises lignin and cellulose and said first aqueous phase comprises at least one sugar having from 5 to 6 carbon atoms, preferably a sugar having 5 carbon atoms, more preferably xylose, and said inorganic acid. Said xylose preferably derives from the acid hydrolysis of hemicellulose. Said sugar having 5 carbon atoms is preferably present in said first aqueous phase in a quantity higher than or equal to 60% by weight with respect to the total weight of sugars contained in said first aqueous phase.

According to a preferred embodiment of the present invention, said second solid phase comprises lignin and said second aqueous phase comprises at least one sugar having from 5 to 6 carbon atoms, preferably a sugar having 6 carbon atoms, more preferably glucose, and said inorganic acid or said enzyme. Said glucose preferably derives from the acid hydrolysis or from the enzymatic hydrolysis of cellulose. Said sugar having 6 carbon atoms is preferably present in said second aqueous phase in a quantity greater than or equal to 80% by weight with respect to the total weight of sugars contained in said second aqueous phase.

The quantity of sugars obtained after acid hydrolysis or enzymatic hydrolysis can be determined by means of techniques known in the art such as, for example, High Performance Liquid Chromatography (HPLC), or Ion Exchange Chromatography: greater details on the determination of the quantity of sugars can be found in the examples provided hereunder.

According to a preferred embodiment of the present invention, said fermentation can be carried out at a temperature ranging from 20° C. to 40° C., preferably ranging from 25° C. to 35° C.

According to a preferred embodiment of the present invention, said fermentation can be carried out for a time ranging from 2 days to 10 days, preferably ranging from 3 days to 8 days.

According to a preferred embodiment of the present invention, said fermentation can be carried out at a pH ranging from 4.5 to 7, preferably ranging from 5 to 6.7. In order to maintain the pH within the desired ranges, an aqueous solution of at least one inorganic base such as, for example, sodium hydroxide, potassium hydroxide, calcium hydroxide, magnesium hydroxide, or mixtures thereof, can be added to the culture medium used for the fermentation, in a quantity which is such as to obtain the desired pH.

According to a preferred embodiment of the present invention, said oleaginous yeast can be selected from: *Rhodotorula glutinis, Rhodotorula gracilis, Rhodotorula graminis, Lypomices starkeyi, Lypomices lipofer, Trigonopsis variabilis, Candida kefyr, Candida curvata, Candida lipolytica, Torulopsis sp., Pichia stipitis.*

According to a preferred embodiment of the present invention, said fermentation is a feed-batch fermentation or a continuous fermentation, preferably continuous. In the case of a continuous fermentation, there is a recirculation of the biomass including at least one polysaccharide.

Before being used in said fermentation, said oleaginous yeast is preferably grown in a culture medium containing xylose, cellobiose, glucose, or mixtures thereof, at a concentration preferably ranging from 1% by weight to 2% by weight with respect to the total weight of said culture medium.

Said fermentation can be advantageously carried out in fermenters known in the art, in the presence of culture mediums normally used for the purpose comprising various nutrients such as, for example, nitrogen, potassium phosphate, magnesium, salts, vitamins.

In order to obtain a greater production of oleaginous cellular biomass, said first aqueous phase or said third aqueous phase can be fed to said fermentation device in two phases.

According to a preferred embodiment of the present invention, said process can comprise feeding a part of said first aqueous phase or of said third aqueous phase to said fermentation device, operating at temperature, pressure and pH indicated above; feeding the remaining part of said first aqueous phase or of said third aqueous phase, at an increasing feeding rate, operating at temperature, pressure and pH indicated above. It should be noted that said feeding rate depends on the dimensions of the fermentation device: in the case of a 20 liters fermentation device, for example, said feeding rate can range from 0.5 l/h (starting feeding rate) to 5 l/h (final feeding rate), preferably ranging from 0.8 l/h (starting feeding rate) to 3.5 l/h (final feeding rate).

According to a preferred embodiment of the present invention, said second aqueous phase or said fourth aqueous phase can be fed to said fermentation device, at an increasing feeding rate, operating at temperature, pressure and pH indicated above. It should be noted that said feeding rate depends on the dimensions of the fermentation device: in the case of a 20 liters fermentation device, for example, said increasing feeding rate can range from 0.1 l/h (starting feeding rate) to 0.4 l/h (final feeding rate), preferably ranging from 0.15 l/h (starting feeding rate) to 0.35 l/h (final feeding rate).

According to a preferred embodiment of the present invention, said microfiltration can be carried out by means of membranes based on regenerated cellulose (for example, membranes known with the commercial name of "Hydrosart® Microfiltration Cassettes" of Sartorius), or by means of ceramic membranes (for example, membranes known with the commercial name of "Ceram inside®" of Tauri).

As indicated above, after feeding said second aqueous phase or said fourth aqueous phase to said fermentation device, the microfiltration of at least a part of said second fermentation broth allows the volume of said second fermentation broth to be kept constant in the fermentation device and to increase the concentration of said second oleaginous cellular biomass in said second fermentation broth, thus allowing lower quantities of biomass including at least one polysaccharide and/or of first solid phase to be subjected to hydrolysis with respect to those normally used.

It should be noted that said microfiltration will be carried out at times and with filtration rates which depend on various parameters such as, for example, the dimensions of the fermentation device, the feeding rate of said second aqueous phase or of said fourth aqueous phase to said fermentation device, the growth rate of the oleaginous cellular biomass. In the case of a 20 liters fermentation device, for example, said microfiltration can be carried out every 30 seconds—5 hours, preferably every 40 seconds—4 hours, for a duration ranging from 1 minute to 10 minutes, preferably ranging from 2 minutes to 8 minutes, for each 24 hours cycle, at a filtration rate ranging from 50 ml/min to 200 ml/min, preferably ranging from 100 ml/min to 180 ml/min.

For the purposes of the present description and of the following claims, the term "retentate" means the second concentrated oleaginous cellular biomass.

For the purposes of the present description and of the following claims, the term "permeate" means the exhausted culture medium.

It should be noted that the retentate is fed to the fermentation device at the same feeding rate as said second aqueous phase or said fourth aqueous phase to said fermentation device.

In order to increase the lipids yield, corn steep liquor can be added to said fermentation device.

According to a preferred embodiment of the present invention, said process additionally comprises adding corn steep liquor to said fermentation device in a quantity ranging from 2 g/l to 20 g/l, preferably ranging from 4 g/l to 18 g/l. Said corn steep liquor can be added either before the feeding of said second aqueous phase, or before the feeding of said fourth aqueous phase.

In order to recover the lipids, said second oleaginous cellular biomass can be subjected to thermal treatment.

According to a preferred embodiment of the present invention, said process also comprises subjecting said second oleaginous cellular biomass comprising lipids to thermal treatment.

Said thermal treatment can be carried out using equipment and techniques known in the art. Said thermal treatment, for example, can be advantageously carried out using pressurized autoclaves (e.g., Brignole autoclave, Mod. AU-2).

According to a preferred embodiment of the present invention, said thermal treatment can be carried out at a pressure ranging from 2 bar to 6.5 bar, preferably ranging from 3 bar to 5.5 bar.

According to a preferred embodiment of the present invention, said thermal treatment can be carried out at a temperature ranging from 100° C. to 160° C., preferably ranging from 110° C. to 150° C.

According to a preferred embodiment of the present invention, said thermal treatment can be carried out for a time ranging from 1 hour to 8 hours, preferably ranging from 2 hours to 5 hours.

At the end of said thermal treatment, the second oleaginous cellular biomass can be recovered by extraction using, for example, a reflux extractor.

According to a preferred embodiment of the present invention, said extraction can be carried out in the present of at least one organic solvent, preferably ethyl acetate.

According to a preferred embodiment of the present invention, said extraction can be carried out at a temperature ranging from 20° C. to 60° C., preferably ranging from 30° C. to 50° C.

According to a preferred embodiment of the present invention, said extraction can be carried out in the present of a quantity of solvent ranging from 2 times to 6 times, preferably from 3 times to 5 times, the quantity of oleaginous cellular biomass obtained from said thermal treatment.

The oleaginous cellular biomass obtained after said thermal treatment can be subjected to extraction once or several times. Said oleaginous cellular biomass is preferably subjected to extraction from once to 5 times, more preferably from once to 3 times.

In order to further concentrate said second oleaginous cellular biomass comprising lipids, said second oleaginous cellular biomass, before being subjected to thermal treatment, can be subjected to centrifugation. Said centrifugation can be carried out for a time ranging from 5 minutes to 30 minutes, preferably from 15 minutes to 25 minutes, at a rotation rate ranging from 3,000 rpm to 9,000 rpm, preferably from 4,000 to 8,000 rpm.

At the end of the above extraction, the following two phases are obtained:
 (i) a solvent phase comprising lipids;
 (ii) a wet solid phase comprising cellular debris and traces of non-separated lipids.

In order to recover the lipids, said solvent phase (i) is subjected to evaporation, obtaining a solid phase comprising lipids.

The process, object of the present invention, allows the lipids to be recovered with a yield ranging from 40% to 98%, preferably from 45% to 95%, said yield being calculated with respect to the total quantity of lipids present in the oleaginous cellular biomass (dry) obtained after fermentation.

The lipids included in said solvent phase (i) are preferably triglycerides, more preferably esters of glycerol with fatty acids having from 14 to 20 carbon atoms such as, for example, palmitic acid, stearic acid, oleic acid, a-linoleic acid, in a quantity higher than or equal to 80% by weight, preferably higher than or equal to 90% by weight, with respect to the total weight of the lipids. Other lipids which can be present in said oily phase are: phospholipids, monoglycerides, diglycerides, or mixtures thereof.

The quantity of lipids contained in the oleaginous cellular biomass obtained after fermentation, as also the quantity of lipids contained in said oily phase, can be determined by means of techniques known in the art such as, for example, the colorimetric method which is based on the reaction of lipids with phosphoric acid and phospho-vanillin: further details relating to this method can be found, for example, in the following article: "Chemical Basis of the Sulpho-phosphovanillin Reaction for Estimating Total Serum Lipids", J. A. Knight et al., published in "Clinical Chemistry" (1972), Vol. 18, No. 3, pages 199-202.

Said wet solid phase (ii) comprising cellular debris, in particular proteins and polysaccharides contained in the cell membrane of the oleaginous yeast used, can be recovered and used in the process, object of the present invention, in particular it can be sent to acid hydrolysis. The proteins and polysaccharides of the membrane are then hydrolyzed to amino acids and simple sugars (for example, glucose, mannose) which can then be used as nitrogen and carbon source in the subsequent fermentation. It should be noted that the recovery and use of said wet solid phase (ii) allows to supply nitrogen to the culture medium used for the fermentation and, consequently, to reduce the quantity of nitrogen normally added to the culture medium in which the fermentation takes place and to provide additional sugars for the fermentation.

According to a preferred embodiment of the present invention, said process also comprises sending said wet solid phase (ii) to acid hydrolysis. In this case, said first aqueous phase, or said second aqueous phase, in addition to said at least one sugar having from 5 to 6 carbon atoms and to said at least one organic acid or to said at least one enzyme, comprise amino acids and simple sugars (for example, glucose, mannose)

deriving from the acid hydrolysis of the proteins and of the polysaccharides of the membrane; whereas said first solid phase or said second solid phase comprise, in addition to cellulose and/or lignin, non-hydrolyzed cellular debris.

In order to obtain a higher yield of lipids (e.g., a yield higher than 98%), said wet solid phase (ii) can be subjected to extraction with a solvent, or with an alcohol/solvent mixture.

According to a preferred embodiment of the present invention, said process also comprises subjecting said aqueous phase (ii) to extraction with at least one solvent which can be selected from aliphatic hydrocarbons having from 3 to 10 carbon atoms such as for example, pentane, n-hexane, octane, or mixtures thereof; or with a mixture comprising at least one aliphatic alcohol having from 3 to 5 carbon atoms which can be selected, for example, from iso-propanol, n-butanol, or mixtures thereof, and at least one aliphatic hydrocarbon having from 3 to 10 carbon atoms selected from those described above. Said organic solvent and/or said mixture, are subsequently evaporated obtaining a further oily phase comprising lipids and a further wet solid phase comprising cellular debris.

As described above for the wet solid phase (ii), said further wet solid phase obtained after said extraction can also be recovered and sent to acid hydrolysis.

The lipids obtained according to the process of the present invention can be subjected to esterification in the presence of at least one alcohol having from 1 to 4 carbon atoms, preferably methanol, ethanol, and at least an acid or base catalyst, in order to produce glycerol and alkyl esters, in particular methyl esters or ethyl esters (biodiesel).

Alternatively, said lipids can be subjected to hydrogenation/deoxygenation in the presence of hydrogen and at least one catalyst in order to produce green diesel. Hydrogenation/deoxygenation processes are known in the art and are described, for example, in European patent application EP 1,728,844.

The present invention will now be illustrated in greater detail through two embodiments with reference to FIGS. 1-2 provided hereunder.

Figure 1:
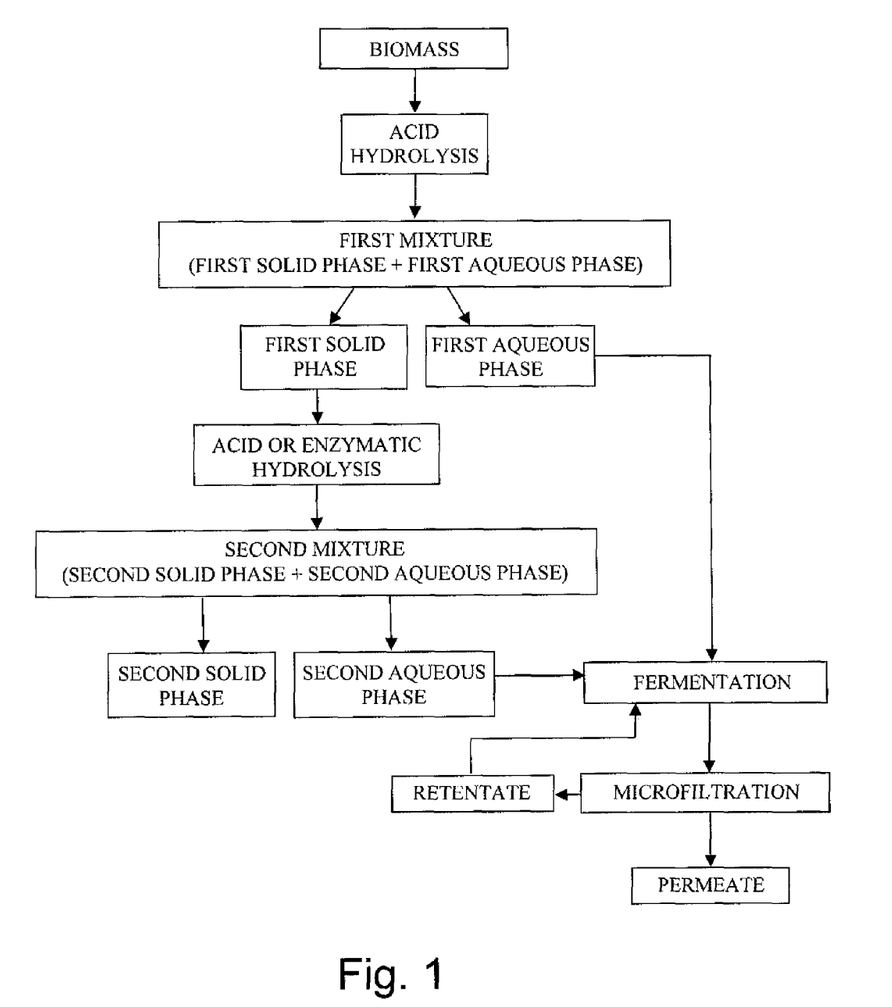

FIG. 1 schematizes a first embodiment of the process object of the present invention. For this purpose, the biomass including at least one polysaccharide (e.g., previously ground lignocellulosic biomass) is subjected to acid hydrolysis in the presence of an aqueous solution of an inorganic acid (e.g., aqueous solution of sulfuric acid at 0.5%), obtaining a first mixture comprising a first aqueous phase including xylose deriving from the hydrolysis of hemicellulose and said inorganic acid, and a first solid phase comprising lignin and cellulose.

Said mixture is subjected to filtration (not represented in FIG. 1) obtaining a first solid phase and a first aqueous phase.

Said first aqueous phase after neutralization (e.g., by the addition of calcium hydroxide) and subsequent filtration (not represented in FIG. 1), is fed to a fermentation device in the presence of an oleaginous yeast (e.g., *Rhodotorula graminis*), obtaining a first fermentation broth comprising a first oleaginous cellular biomass (not represented in FIG. 1).

Said first solid phase is subjected to hydrolysis (e.g., in the presence of an aqueous solution of an inorganic acid, or of an aqueous solution of an enzyme), obtaining a second mixture comprising a second aqueous phase including glucose deriving from the hydrolysis of cellulose and said inorganic acid or said enzyme, and a second solid phase including lignin.

Said mixture is subjected to filtration (not represented in FIG. 1) obtaining a second solid phase and a second aqueous phase.

Said second aqueous phase, after neutralization (e.g., by the addition of calcium hydroxide) and subsequent filtration (not represented in FIG. 1), is fed to the above fermentation device in the presence of said first fermentation broth comprising a first oleaginous cellular biomass obtaining a second fermentation broth comprising a second oleaginous cellular biomass including lipids (not represented in FIG. 1). Part of said second fermentation broth is subjected to microfiltration (e.g., by sampling, through a peristaltic pump which is activated every hour, for 4 minutes, for each 24 hours cycle, operating at a filtration rate of 150 ml/min) obtaining a retentate (i.e. second concentrated oleaginous cellular biomass) which is fed to said fermentation device, and a permeate (i.e. exhausted culture medium) which is eliminated.

Figure 2:
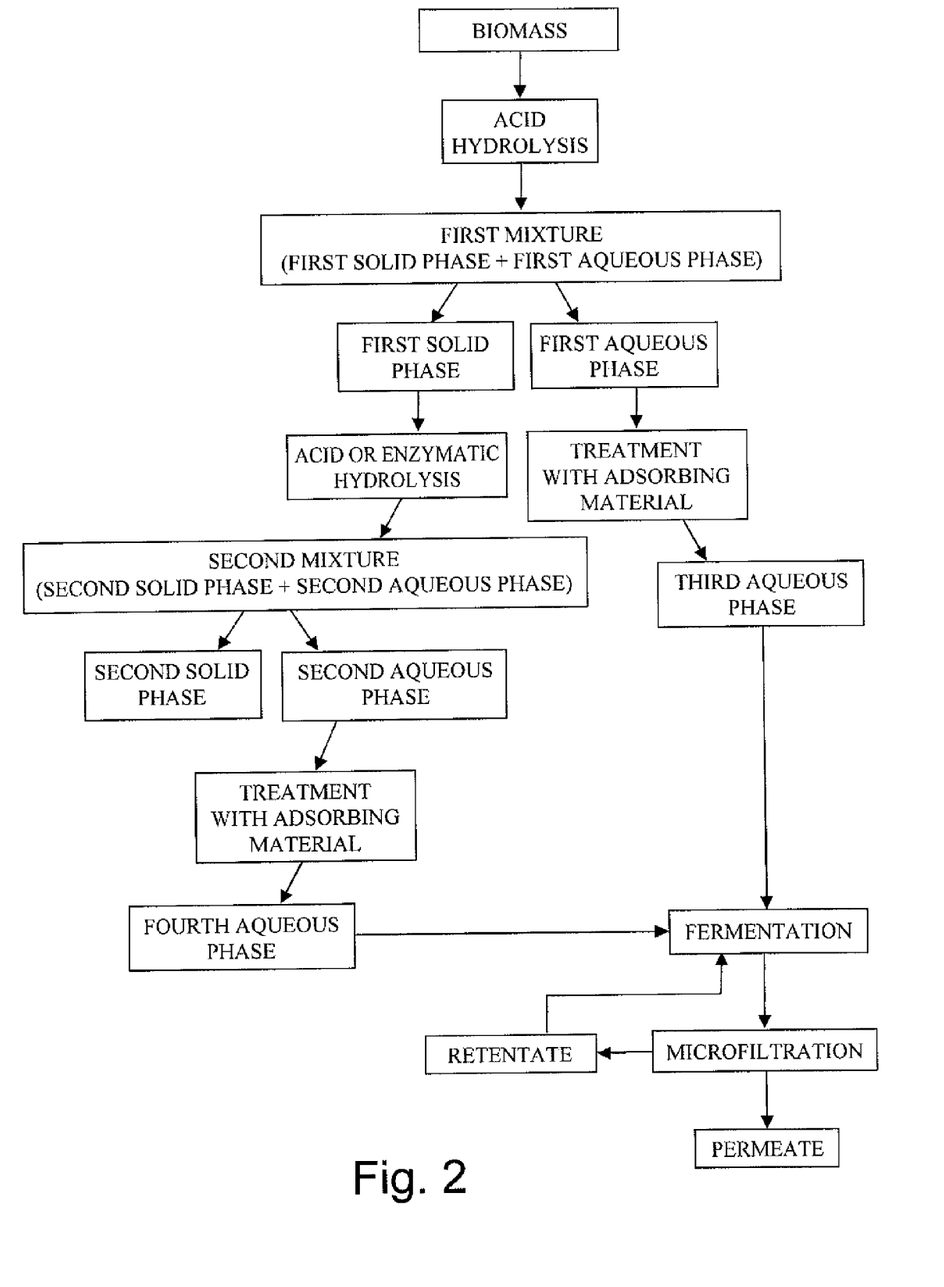

FIG. 2 schematizes a second embodiment of the process, object of the present invention. For this purpose, the biomass including at least one polysaccharide (e.g., previously ground lignocellulosic biomass) is subjected to acid hydrolysis in the presence of an aqueous solution of an inorganic acid (e.g., aqueous solution of sulfuric acid at 0.5%), obtaining a first mixture comprising a first aqueous phase including xylose deriving from the hydrolysis of hemicellulose and said inorganic acid, and a first solid phase comprising lignin and cellulose.

Said mixture is subjected to filtration (not represented in FIG. 2) obtaining a first solid phase and a first aqueous phase.

Said first aqueous phase, after neutralization (e.g., by the addition of calcium hydroxide) and subsequent filtration (not represented in FIG. 2), is subjected to a treatment with at least one adsorbing material (e.g., zeolite CBV28014-Zeolyst) obtaining a third aqueous phase.

Said third aqueous phase is fed to a fermentation device in the presence of an oleaginous yeast (e.g., *Rhodotorula graminis*), obtaining a first fermentation broth comprising a first oleaginous cellular biomass (not represented in FIG. 2).

Said first solid phase is subjected to hydrolysis (e.g., in the presence of an aqueous solution of an inorganic acid, or of an aqueous solution of an enzyme), obtaining a second mixture comprising a second aqueous phase including glucose deriving from the hydrolysis of cellulose and said inorganic acid or said enzyme, and a second solid phase including lignin.

Said mixture is subjected to filtration (not represented in FIG. 2) obtaining a second solid phase and a second aqueous phase.

Said second aqueous phase, after neutralization (e.g., by the addition of calcium hydroxide) and subsequent filtration (not represented in FIG. 2), is subjected to a treatment with at least one adsorbing material (e.g., zeolite CBV28014-Zeolyst) obtaining a fourth aqueous phase.

Said fourth aqueous phase is fed to the above fermentation device in the presence of said first fermentation broth comprising a first oleaginous cellular biomass obtaining a second fermentation broth comprising a second oleaginous cellular biomass including lipids (not represented in FIG. 2). Part of said second fermentation broth is subjected to microfiltration (e.g., by sampling, through a peristaltic pump which is activated every hour, for 4 minutes, for each 24 hours cycle, operating at a filtration rate of 150 ml/min) obtaining a retentate (i.e. second concentrated oleaginous cellular biomass) which is fed to said fermentation device, and a permeate (i.e. exhausted culture medium) which is eliminated.

Some illustrative and non-limiting examples are provided for a better understanding of the present invention and for its embodiment.

EXAMPLE 1

Acid Hydrolysis 4 kg of poplar sawdust (particle diameter <1 mm) were added to 22.8 liters of an aqueous solution of sulfuric acid at 0.5%.

The composition of the starting lignocellulosic biomass was the following: 50% by weight of cellulose, 25% by weight of hemicellulose, 25% by weight of lignin, with respect to the total weight of the starting lignocellulosic biomass.

The reaction mixture thus obtained was kept under stirring in a reactor, at 180° C., for 10 minutes, obtaining a first mixture comprising a first solid phase (including cellulose and lignin) and a first aqueous phase (including sugars and sulfuric acid).

Said first reaction mixture was discharged from the reactor and subjected to filtration and the following products were obtained: 2.7 kg (dry weight) of a first solid phase (comprising cellulose and lignin) and 22 liters of a first aqueous phase (comprising 51 g/l of sugars of which 33 g/l of xylose deriving from the acid hydrolysis of hemicellulose and 9 g/l of glucose deriving from the acid hydrolysis of cellulose, and sulfuric acid).

Said first aqueous phase was subjected to neutralization, in a stirred reactor, by the addition of calcium hydroxide, until a pH equal to 6.5 was reached, and subsequently subjected to filtration, in order to eliminate the salt (i.e. calcium sulfate) which had been formed. 1.1 kg of zeolite CBV28014 (MFI type with a Si/Al ratio=140) of Zeolyst International were then added to said first aqueous phase, in a stirred reactor. The suspension obtained was left, under stirring, at 25° C., at atmospheric pressure (1 bar), for 4 hours, and subsequently filtered to separate the zeolite, obtaining 22 liters of a third aqueous phase having a content of furfural and of hydroxymethylfurfural lower than 0.1 g/l and a content of sugars equal to 46.41 g/l of which 30 g/l of xylose and 8.3 g/l of glucose.

The content of furfural and of hydroxymethylfurfural was determined by High Performance Liquid Chromatography (HPLC) using a Zorbax Bonus RP column (100 mm×2.1 mm, 3.5 μm) of Agilent, with a movable phase 0.01 mM of acetic acid in an aqueous solution of formic acid at 0.2%.

The sugar content was determined by Ion-Exchange Chromatography (HPAE-PAD), using a Dionex chromatograph, equipped with a Carbopac PA100 column, with a gradient of sodium hydroxide and sodium acetate as counter-ion.

18.4 liters of an aqueous solution of sulfuric acid at 0.5% were added to the above 2.7 kg of said first solid phase.

The reaction mixture thus obtained was kept, under stirring, in a reactor, at 230° C., for 1 minute, obtaining a second mixture comprising a second solid phase (comprising lignin) and a second aqueous phase (comprising sugars and sulfuric acid).

Said second reaction mixture was discharged from the reactor and subjected to filtration and the following products were obtained: 1.2 kg (dry weight) of a second solid phase (comprising lignin) and 18 liters of a second aqueous phase (comprising 53 g/l of sugars of which 52 g/l of glucose deriving from the acid hydrolysis of cellulose, and sulfuric acid).

Said second aqueous phase was subjected to neutralization, in a stirred reactor, by the addition of calcium hydroxide, until a pH equal to 6.5 was reached, and subsequently subjected to filtration, in order to eliminate the salt (i.e. calcium sulfate) which had been formed. 1.1 kg of zeolite CBV28014 (MFI type with a Si/Al ratio=140) of Zeolyst International were then added to said second aqueous phase, in a stirred reactor. The suspension obtained was left, under stirring, at 25° C., at atmospheric pressure (1 bar), for 4 hours, and subsequently filtered to separate the zeolite, obtaining 18 liters of a fourth aqueous phase having a content of furfural and of hydroxymethylfurfural lower than 0.1 g/l (said content was measured as described above) and a content of sugars equal to 48.23 g/l of which 47 g/l of glucose and traces of other sugars (said content was determined as described above).

Fermentation

The fermentation was carried out in a 20 liters fermenter.

For this purpose, the strain of *Rhodotorula graminis* DBVPT 4620 was grown in YEPG medium for yeasts containing 2% by weight of glucose, in a 0.5 litre flask, for a night, under stirring (170 rpm), at 30° C., reaching a concentration equal to 0.1 g/l (dry weight). Said culture was used as inoculum.

The inoculum obtained as described above was fed to the above fermenter together with 8 liters of said third aqueous phase obtained as described above.

The cells of *Rhodotorula graminis* DBVPG 4620 were grown, under stirring, at 500 rpm, at 30° C., aeration 1 l/min per litre of culture of sterile air, at pH equal to 5.5, for 36 hours, obtaining 124 g of a first oleaginous cellular biomass (concentration equal to 15 g/l—dry weight).

The remaining 14 liters of said third aqueous phase were then fed (feed-batch feeding) to said fermenter containing said first culture broth comprising a first oleaginous cellular biomass, at an increasing feeding rate ranging from 0.9 l/h (starting feeding rate) to 2.5 l/h (final feeding rate), obtaining a culture volume, after 44 hours, under the same operative conditions indicated above, equal to 20 liters. At the end, 413 g of a first oleaginous cellular biomass were obtained [concentration equal to 20.2 g/l (dry weight)].

18 liters of said fourth aqueous phase obtained as described above were fed, in continuous, to said fermenter, maintaining the volume of fermentation broth constantly at 20 liters, with an increasing feeding rate ranging from 0.19 l/h (starting feeding rate) to 0.31 l/h (final feeding rate). The whole mixture was kept under stirring at 500 rpm, at 30° C., aeration 1 l/min per litre of culture of sterile air, at pH equal to 5.5, for 76 hours.

A microfiltration apparatus was connected to the fermenter, by means of a peristaltic pump, equipped with a microfiltration membrane "Hydrosart® Microfiltration Cassettes" of Sartoriuos, in order to eliminate the exhausted culture medium (permeate) and concentrate the second oleaginous cellular biomass (retentate) produced in said second culture broth. For this purpose, said peristaltic pump was activated every hour, for 4 minutes, for each 24 hours cycle, removing part of said second culture broth comprising said second oleaginous cellular biomass, operating at a filtration rate equal to 150 ml/min. Said second oleaginous cellular biomass was thus concentrated 5 times obtaining a retentate (i.e. second concentrated oleaginous cellular biomass) which was fed to the fermenter with a feeding rate equal to 0.31 l/h, and a permeate (i.e. exhausted culture medium) which was eliminated.

At the end of the fermentation, the yeast cells were collected and centrifuged at 7,000 rpm, for 20 minutes, obtaining 1,500 g of said second oleaginous cellular biomass [760 g (dry weight)—concentration equal to 38 g/l (dry weight)].

Recovery of the Lipids

The recovery of the lipids was carried out in a 2 liters Brignole autoclave Mod. AU-2.

For this purpose, 1,500 g [760 g (dry weight)] of oleaginous cellular biomass obtained as described above, were fed to the above autoclave kept at a pressure equal to 4.9 bar and at a temperature equal to 140° C., for 4 hours.

After 4 hours under the above conditions, 1,410 g [714 g (dry weight)] of oleaginous cellular biomass were discharged from the autoclave. Said oleaginous cellular biomass was subjected to two extraction cycles, 2 hours for each cycle, in a reflux extractor equipped with a thermostat, at a temperature equal to 45° C., in the presence of ethyl acetate (volume of ethyl acetate equal to 4 times the weight of said oleaginous cellular biomass) obtaining: (i) a solvent phase comprising lipids and (ii) a wet solid phase comprising cellular debris and traces of non-separated lipids.

Said solvent phase (i) and said wet solid phase (ii) were separated by filtration.

Said solvent phase (i) was subjected to determination of the lipid content. The total content of lipids obtained proved to be equal to 342 g [recovery yield equal to 92% calculated with respect to the total quantity of lipids present in said second oleaginous cellular biomass (dry) obtained after fermentation].

The lipid content was determined using the colorimetric method which is based on the reaction of lipids with phosphoric acid and phospho-vanillin.

Said wet solid phase (ii) proved to comprise water and cellular debris, including 42% by weight (dry weight) of polysaccharides and 45% by weight of proteins (dry weight).

The content of polysaccharides was determined by spectrophotometric reading using the Fehling method; the protein content was determined by means of the Bradford method.

EXAMPLE 2

Acid Hydrolysis 4 kg of poplar sawdust (particle diameter <1 mm) were added to 22.8 liters of an aqueous solution of sulfuric acid at 0.5%.

The composition of the starting lignocellulosic biomass was the following: 50% by weight of cellulose, 25% by weight of hemicellulose, 25% by weight of lignin, with respect to the total weight of the starting lignocellulosic biomass.

The reaction mixture thus obtained was kept under stirring in a reactor, at 180° C., for 10 minutes, obtaining a first mixture comprising a first solid phase (including cellulose and lignin) and a first aqueous phase (including sugars and sulfuric acid).

Said first reaction mixture was discharged from the reactor and subjected to filtration and the following products were obtained: 2.7 kg (dry weight) of a first solid phase (comprising cellulose and lignin) and 22 liters of a first aqueous phase (comprising 51 g/l of sugars of which 33 g/l of xylose deriving from the acid hydrolysis of hemicellulose and 9 g/l of glucose deriving from the acid hydrolysis of cellulose, and sulfuric acid).

Said first aqueous phase was subjected to neutralization, in a stirred reactor, by the addition of calcium hydroxide, until a pH equal to 6.5 was reached, and subsequently subjected to filtration, in order to eliminate the salt (i.e. calcium sulfate) which had been formed. 1.1 kg of zeolite CBV28014 (MFI type with a Si/Al ratio=140) of Zeolyst International were then added to said first aqueous phase, in a stirred reactor. The suspension obtained was left, under stirring, at 25° C., at atmospheric pressure (1 bar), for 4 hours, and subsequently filtered to separate the zeolite, obtaining 22 liters of a third aqueous phase having a content of furfural and of hydroxymethylfurfural lower than 0.1 g/l and a content of sugars equal to 46.41 g/l of which 30 g/l of xylose and 8.3 g/l of glucose.

The content of furfural and of hydroxymethylfurfural was determined by High Performance Liquid Chromatography (HPLC) using a Zorbax Bonus RP column (100 mm×2.1 mm, 3.5 μm) of Agilent, with a movable phase 0.01 mM of acetic acid in an aqueous solution of formic acid at 0.2%.

The sugar content was determined by Ion-Exchange Chromatography (HPAE-PAD), using a Dionex chromatograph, equipped with a Carbopac PA100 column, with a gradient of sodium hydroxide and sodium acetate as counter-ion.

18.4 liters of an aqueous solution of sulfuric acid at 0.5% were added to the above 2.7 kg of said first solid phase.

The reaction mixture thus obtained was kept, under stirring, in a reactor, at 230° C., for 1 minute, obtaining a second mixture comprising a second solid phase (comprising lignin) and a second aqueous phase (comprising sugars and sulfuric acid).

Said second reaction mixture was discharged from the reactor and subjected to filtration and the following products were obtained: 1.2 kg (dry weight) of a second solid phase (comprising lignin) and 18 liters of a second aqueous phase (comprising 53 g/l of sugars of which 52 g/l of glucose deriving from the acid hydrolysis of cellulose, and sulfuric acid).

Said second aqueous phase was subjected to neutralization, in a stirred reactor, by the addition of calcium hydroxide, until a pH equal to 6.5 was reached, and subsequently subjected to filtration, in order to eliminate the salt (i.e. calcium sulfate) which had been formed. 1.1 kg of zeolite CBV28014 (MFI type with a Si/Al ratio=140) of Zeolyst International were then added to said second aqueous phase, in a stirred reactor. The suspension obtained was left, under stirring, at 25° C., at atmospheric pressure (1 bar), for 4 hours, and subsequently filtered to separate the zeolite, obtaining 18 liters of a fourth aqueous phase having a content of furfural and of hydroxymethylfurfural lower than 0.1 g/l (said content was measured as described above) and a content of sugars equal to 48.23 g/l of which 47 g/l of glucose and traces of other sugars (said content was determined as described above).

Fermentation

The fermentation was carried out in a 20 liters fermenter.

For this purpose, the strain of *Rhodotorula graminis* DBVPG 4620 was grown in YEPG medium for yeasts containing 2% by weight of glucose, in a 0.5 litre flask, for a night, under stirring (170 rpm), at 30° C., reaching a concentration equal to 0.1 g/l (dry weight). Said culture was used as inoculum.

15 g/l of corn steep liquor were added to said 22 liters of third aqueous phase obtained as described above.

The inoculum obtained as described above was fed to the above fermenter together with 8 liters of said third aqueous phase containing corn steep liquor.

The cells of *Rhodotorula graminis* DBVPT 4620 were grown, under stirring, at 500 rpm, at 30° C., aeration 1 l/min per litre of culture of sterile air, at pH equal to 5.5, for 36 hours, obtaining 124 g of a first oleaginous cellular biomass (concentration equal to 15 g/l—dry weight).

The remaining 14 liters of said third aqueous phase containing corn steep liquor were then fed (feed-batch feeding) to said fermenter containing said first culture broth comprising a first oleaginous cellular biomass, at an increasing feeding rate ranging from 0.9 l/h (starting feeding rate) to 2.5 l/h (final feeding rate), obtaining a culture volume, after 44 hours, under the same operative conditions indicated above, equal to 20 liters. At the end, 429 g of a first oleaginous cellular biomass were obtained [concentration equal to 23.55 g/l (dry weight)].

18 liters of said fourth aqueous phase obtained as described above were fed, in continuous, to said fermenter, maintaining the volume of fermentation broth constantly at 20 liters, with an increasing feeding rate ranging from 0.19 l/h (starting feeding rate) to 0.31 l/h (final feeding rate). The whole mixture was kept under stirring at 500 rpm, at 30° C., aeration 1 l/min per litre of culture of sterile air, at pH equal to 5.5, for 76 hours.

A microfiltration apparatus was connected to the fermenter, by means of a peristaltic pump, equipped with a microfiltration membrane "Hydrosart® Microfiltration Cassettes" of Sartoriuos, in order to eliminate the exhausted culture medium (permeate) and concentrate the second oleaginous cellular biomass (retentate) produced in said second culture broth. For this purpose, said peristaltic pump was activated every hour, for 4 minutes, for each 24 hours cycle, removing part of said second culture broth comprising said second oleaginous cellular biomass, operating at a filtration rate equal to 150 ml/min. Said second oleaginous cellular biomass was thus concentrated 5 times obtaining a retentate (i.e. second concentrated oleaginous cellular biomass) which was fed to the fermenter with a feeding rate equal to 0.31 l/h, and a permeate (i.e. exhausted culture medium) which was eliminated.

At the end of the fermentation, the yeast cells were collected and centrifuged at 7,000 rpm, for 20 minutes, obtaining 1,560 g of said second oleaginous cellular biomass [790 g (dry weight)—concentration equal to 39.5 g/l (dry weight)].

Recovery of the Lipids

The recovery of the lipids was carried out in a 2 liters Brignole autoclave Mod. AU-2.

For this purpose, 1,560 g [790 g (dry weight)] of oleaginous cellular biomass obtained as described above, were fed to the above autoclave kept at a pressure equal to 4.9 bar and at a temperature equal to 140° C., for 4 hours.

After 4 hours under the above conditions, 1,466 g [742 g (dry weight)] of oleaginous cellular biomass were discharged from the autoclave. Said oleaginous cellular biomass was subjected to two extraction cycles, 2 hours for each cycle, in a reflux extractor equipped with a thermostat, at a temperature equal to 45° C., in the presence of ethyl acetate (volume of ethyl acetate equal to 4 times the weight of said oleaginous cellular biomass) obtaining: (i) a solvent phase comprising lipids and (ii) a wet solid phase comprising cellular debris and traces of non-separated lipids.

Said solvent phase (i) and said wet solid phase (ii) were separated by filtration.

Said solvent phase (i) was subjected to determination of the lipid content. The total content of lipids obtained proved to be equal to 418 g [recovery yield equal to 94% calculated with respect to the total quantity of lipids present in said second oleaginous cellular biomass (dry) obtained after fermentation].

The lipid content was determined using the colorimetric method which is based on the reaction of lipids with phosphoric acid and phospho-vanillin.

Said wet solid phase (ii) proved to comprise water and cellular debris, including 42% by weight (dry weight) of polysaccharides and 45% by weight of proteins (dry weight).

The content of polysaccharides was determined by spectrophotometric reading using the Fehling method; the protein content was determined by means of the Bradford method.

The invention claimed is:

1. A process for the production of lipids from biomass including at least one polysaccharide comprising:
    subjecting said biomass, including at least one polysaccharide to acid hydrolysis obtaining a first mixture comprising a first solid phase and a first aqueous phase;
    feeding said first aqueous phase to a fermentation device in the presence of at least one oleaginous yeast obtaining a first fermentation broth comprising a first oleaginous cellular biomass;
    subjecting said first solid phase to acid hydrolysis or to enzymatic hydrolysis obtaining a second mixture comprising a second solid phase and a second aqueous phase;
    feeding said second aqueous phase to said fermentation device in the presence of said first fermentation broth obtaining a second fermentation broth comprising a second oleaginous cellular biomass including lipids;
    subjecting at least a part of said second fermentation broth to microfiltration obtaining a retentate and a permeate; and
    feeding said retentate to said fermentation device.

2. The process for the production of lipids from biomass including at least one polysaccharide according to claim 1, wherein said biomass including at least one polysaccharide is a lignocellulosic biomass.

3. The process for the production of lipids from biomass including at least one polysaccharide according to claim 1, wherein said biomass including at least one polysaccharide is subjected to a preliminary grinding process before being subjected to said acid hydrolysis.

4. The process for the production of lipids from biomass including at least one polysaccharide according to claim 1, wherein said acid hydrolysis is carried out in the presence of at least one inorganic acid.

5. The process for the production of lipids from biomass including at least one polysaccharide according to claim 1, wherein said biomass including at least one polysaccharide or said first solid phase are present in the reaction mixture in a quantity ranging from 5% by weight to 20% by weight with respect to the total weight of the reaction mixture.

6. The process for the production of lipids from biomass including at least one polysaccharide according to claim 4, wherein said inorganic acid is selected from the group consisting of: sulfuric acid, nitric acid, hydrochloric acid, phosphoric acid, and mixtures thereof.

7. The process for the production of lipids from biomass including at least one polysaccharide according to claim 4, wherein said inorganic acid is present in an aqueous solution at a concentration ranging from 0.1% by weight to 2% by weight with respect to the total weight of the aqueous solution.

8. The process for the production of lipids from biomass including at least one polysaccharide according to claim 1, wherein said acid hydrolysis is carried out at a temperature ranging from 140° C. to 270° C.

9. The process for the production of lipids from biomass including at least one polysaccharide according to claim 1, wherein said acid hydrolysis is carried out for a time ranging from 10 seconds to 30 minutes.

10. The process for the production of lipids from biomass including at least one polysaccharide according to claim 1, wherein said first aqueous phase and/or said second aqueous phase are subjected to a treatment with at least one adsorbing material obtaining a third aqueous phase and/or a fourth aqueous phase, respectively.

11. The process for the production of lipids from biomass including at least one polysaccharide according to claim 1, wherein, before being fed to said fermentation device, said first aqueous phase and/or said second aqueous phase are subjected to neutralization by the addition of at least one oxide and/or of at least one hydroxide, such as calcium oxide, calcium hydroxide or barium hydroxide, or mixtures thereof.

12. The process for the production of lipids from biomass including at least one polysaccharide according to claim 10, wherein said treatment with at least one adsorbing material is carried out at a temperature ranging from 10° C. to 150° C.

13. The process for the production of lipids from biomass including at least one polysaccharide according to claim 10, wherein said treatment with at least one adsorbing material is carried out at a pressure ranging from 0.5 bar to 10 bar.

14. The process for the production of lipids from biomass including at least one polysaccharide according to claim 10, wherein said treatment with at least one adsorbing material is carried out for a time ranging from 10 minutes to 6 hours.

15. The process for the production of lipids from biomass including at least one polysaccharide according to claim 10, wherein said adsorbing material is selected from crystalline microporous silicates or metal silicates of the zeolite type having MFI, MOR, FAU or BEA structures.

16. The process for the production of lipids from biomass including at least one polysaccharide according to claim 10, wherein said adsorbing material is added to said first aqueous phase and/or to said second aqueous phase in a quantity ranging from 0.5% by weight to 50% by weight with respect to the total weight of said first aqueous phase or of said second aqueous phase.

17. The process for the production of lipids from biomass including at least one polysaccharide according to claim 1, wherein said fermentation is carried out at a temperature ranging from 20° C. to 40° C.

18. The process for the production of lipids from biomass including at least one polysaccharide according to claim 1, wherein said fermentation is carried out for a time ranging from 2 days to 10 days.

19. The process for the production of lipids from biomass including at least one polysaccharide according to claim 1, wherein said fermentation is carried out at a pH ranging from 4.5 to 7.

20. The process for the production of lipids from biomass including at least one polysaccharide according to claim 1, wherein said oleaginous yeast can be selected from: *Rhodotorula glutinis, Rhodotorula gracilis, Rhodotorula graminis, Lypomices starkeyi, Lypomices lipofer, Trigonopsis variabilis, Candida kefyr, Candida curvata, Candida lipolytica, Torulopsis sp., Pichia stipitis*.

21. The process for the production of lipids from biomass including at least one polysaccharide according to claim 1, wherein said microfiltration is carried out by means of membranes based on regenerated cellulose, or by means of ceramic membranes.

22. The process for the production of lipids from biomass including at least one polysaccharide according to claim 1, wherein said process comprises adding corn steep liquor to said fermentation device in a quantity ranging from 2 g/l to 20 g/l.

23. The process for the production of lipids from biomass including at least one polysaccharide according to claim 1, wherein said process comprises subjecting said second oleaginous cellular biomass including lipids to thermal treatment.

24. The process for the production of lipids from biomass including at least one polysaccharide according to claim 23, wherein said thermal treatment is carried out at a pressure ranging from 2 bar to 6.5 bar.

25. The process for the production of lipids from biomass including at least one polysaccharide according to claim 23, wherein said thermal treatment is carried out at a temperature ranging from 100° C. to 160° C.

26. The process for the production of lipids from biomass including at least one polysaccharide according to claim 23, wherein said thermal treatment is carried out for a time ranging from 1 hr to 8 hrs.

27. The process for the production of lipids from biomass including at least one polysaccharide according to claim 23, wherein at the end of said thermal treatment the oleaginous cellular biomass is subjected to extraction, in the presence of at least one organic solvent.

28. Biodiesel or green diesel obtained from the lipids produced through the process according to claim 1.

29. The process for the production of lipids from biomass including at least one polysaccharide according to claim 10, wherein before being subjected to said treatment with at least one adsorbing material, said first aqueous phase and/or said second aqueous phase are subjected to neutralization by the addition of at least one oxide and/or of at least one hydroxide.

30. The process for the production of lipids from biomass including at least one polysaccharide according to claim 27, wherein the at least one organic solvent is ethyl acetate.

* * * * *